(12) United States Patent
Bove et al.

(10) Patent No.: US 6,293,900 B1
(45) Date of Patent: Sep. 25, 2001

(54) MAGNETIC FACE MASK

(75) Inventors: Anthony Bove, Port Jefferson; Vincent Ardizzone, Bay Shore, both of NY (US)

(73) Assignee: Nu-Magnetics, Inc., Port Jefferson, NY (US)

( * ) Notice: Subject to any disclaimer, the term of this patent is extended or adjusted under 35 U.S.C. 154(b) by 0 days.

(21) Appl. No.: 08/911,950

(22) Filed: Aug. 15, 1997

Related U.S. Application Data

(63) Continuation-in-part of application No. 08/678,348, filed on Jul. 11, 1996, now Pat. No. 5,871,438, which is a continuation of application No. 08/573,390, filed on Dec. 15, 1995, now Pat. No. 5,538,495, which is a continuation of application No. 08/427,733, filed on Apr. 24, 1995, now Pat. No. 5,514,072, which is a continuation of application No. 08/276,876, filed on Jul. 18, 1994, now abandoned, which is a continuation of application No. 08/158,607, filed on Nov. 29, 1993, now abandoned, which is a continuation of application No. 07/990,927, filed on Dec. 14, 1992, now Pat. No. 5,277,692, which is a continuation of application No. 07/823,149, filed on Jan. 21, 1992, now abandoned.

(51) Int. Cl.$^7$ .................................................. A61N 1/00
(52) U.S. Cl. ............................................................ 600/15
(58) Field of Search .................................... 600/9–15

(56) References Cited

U.S. PATENT DOCUMENTS

| | | |
|---|---|---|
| 1,820,602 | 8/1931 | Dick . |
| 2,028,889 | 1/1936 | Baddour . |
| 2,191,080 | 2/1940 | Lewis ................... 128/380 |
| 2,252,423 | 8/1941 | Baddour ................ 219/46 |
| 2,433,233 | 12/1947 | Meminger ............. 128/380 |
| 3,971,387 | 7/1976 | Mantell ................. 128/410 |
| 4,330,892 | 5/1982 | Fukushima ............... 5/437 |
| 4,549,532 | * 10/1985 | Baermann ............... 600/15 |
| 5,092,835 | 3/1992 | Schurig et al. ........... 600/9 |
| 5,169,380 | 12/1992 | Brennan ................. 600/26 |
| 5,277,692 | * 1/1994 | Ardizzone ............... 600/15 |
| 5,304,111 | * 4/1994 | Mitsuno et al. .......... 600/15 |
| 5,389,981 | 2/1995 | Riach, Jr. ............... 351/158 |
| 5,415,617 | 5/1995 | Kraus ................... 600/13 |
| 5,441,495 | 8/1995 | Liboff et al. ............. 600/9 |
| 5,527,357 | 6/1996 | Springer, Jr. ........... 607/140 |
| 5,738,624 | * 4/1998 | Zablotsky ............... 600/15 |

FOREIGN PATENT DOCUMENTS

| | | | |
|---|---|---|---|
| 2575926 | * 7/1986 | (FR) | .................... 600/15 |
| 2583292 | * 12/1986 | (FR) | .................... 600/15 |

* cited by examiner

Primary Examiner—John P. Lacyk
(74) Attorney, Agent, or Firm—Cislo & Thomas, LLP

(57) ABSTRACT

An eye mask or face mask incorporating sources of spatially alternating yet static magnetic fields provides magnetotherapy to the eyes and/or face. In one embodiment, an eye mask is provided that has an opaque eye plate and opaque rearwardly projecting cushion about its perimeter. A sheet of alternating magnetic material provides alternating magnetic fields when travel is made in any direction. The eye mask may be attached to the face by elastic straps or other means which may be adjusted for comfort. The perimeter cushion serves to hold the eye mask away from the eyes and projecting eyelashes of the wearer so that greater comfort is achieved. The opaque nature of both the eye plate and the cushion serves to keep light out, allowing the eyes to enjoy a dark environment, especially appropriate for sleep. The eye mask may be worn during lengthy periods of repose such as sleeping. In an alternative embodiment, a face mask incorporating alternating magnetic field forces may have optional eye apertures as well as nose and mouth apertures. Elastic straps serve to hold the face mask to the wearer's face. Alternative embodiments of sources of alternating magnetic fields may be achieved through the use of magnets in a triangular or square checkerboard pattern or alternating patterns of circle-centered toroids having alternating magnetic fields.

7 Claims, 7 Drawing Sheets

|   |   |   |   |   |
|---|---|---|---|---|
| N | S | N | S | N |
| S | N | S | N | S |
| N | S | N | S | N |
| S | N | S | N | S |
| N | S | N | S | N |

FIG.5

MAGNETIC FACE MASK

CROSS-REFERENCES TO RELATED APPLICATIONS

This application is a continuation-in-part application of U.S. patent application Ser. No. 08/678,348 filed Jul. 11, 1996 now U.S. Pat. No. 5,871,438, which is a continuation of application Ser. No. 08/573,390, filed Dec. 15, 1995, now U.S. Pat. No. 5,538,495 which is a continuation of application Ser. No. 08/427,733, filed Apr. 24, 1995, now U.S. Pat. No. 5,514,072, which is a continuation of application Ser. No. 08/276,876, filed Jul. 18, 1994, now abandoned, which is a continuation of application Ser. No. 08/158,607, filed Nov. 29, 1993, now abandoned, which is a continuation of application Ser. No. 07/990,927, filed Dec. 14, 1992, now U.S. Pat. No. 5,277,692, which is a continuation of application Ser. No. 07/823,149, filed Jan. 21, 1992, now abandoned. The contents of all applications of which the present application is a divisional, continuation, continuation-in-part, or otherwise from which this application is related are incorporated herein by this reference thereto.

BACKGROUND OF THE INVENTION

1. Field of the Invention

This invention relates to magneto-therapeutic devices, and more particularly to eye and face masks incorporating static magnetic field generators in the form of magnets to provide magneto-therapy.

2. Description of the Related Art

Magneto-therapy uses magnetic fields to provide therapeutic and restorative treatment to limbs, organs, and other parts of the body. Generally, one means by which magneto-therapy may be achieved is by bringing a magnet or series of magnets into close proximity with the affected body part or organ of interest. As is known according to Faraday's Law of Magnetic Induction, as well as the Hall Effect, charged particles experience a force acting on them when they move through a magnetic field in a perpendicular direction. Since human blood is replete with ions and electrolytes, it has many charged particles which experience a force, including an aligning force, when moving through a magnetic field. When exposed and caused to so travel through a magnetic field, such ions and electrolytes may generate heat, causing the associated blood vessel to widen. The widening of the blood vessel would then allow increased volumes of blood to flow through the blood vessel.

Additional therapeutic or restorative effects might arise through the alignment of polar molecules as they pass through the magnetic field. When passing through a magnetic field, polar molecules rotate to align themselves with the field. Such alignment would alternate with the magnetic polarity as the polar molecules traveled through different regions of such magnetic polarity. The mechanical motion of the rotation of such polar molecules might also cause heating and the like and would also stimulate, mix, or agitate the blood in a gentle manner, causing it to gently churn. Such mixing of the blood at the molecular level may cause it to more easily recognize foreign matter. By recognizing foreign matter, the blood and/or immune system may be able to more readily address such foreign matter.

Several patents are known having various designs for the alternation of magnets of different polarity to provide spatially diverse magnetic fields. The patent to Latzke (U.S. Pat. No. 4,489,711 issued Dec. 25, 1984) and the patents to Ardizzone (U.S. Pat. No. 5,277,692 issued Jan. 11, 1994; U.S. Pat. No. 5,514,072 issued May 7, 1996; and U.S. Pat. No. 5,538,495 issued Jul. 23, 1996) all disclose a variety of magnetic plaster and magnetic pads having certain magnetic geometries in order to achieve spatially varying magnetic fields through the use of magnets.

While certain portions of the human body have been emphasized as being subject to the use of magneto-therapeutic devices, it remains to be seen in the art to provide an eye or face mask that would incorporate magneto-therapeutic elements. It can be seen, therefore, that it would be of some advantage to provide magnetic-therapeutic aid to a person's eyes and/or face, particularly while the person rests or sleeps as such magneto-therapeutic treatment could then be effected for a period of several hours without interfering with a person's daily and ongoing activities.

SUMMARY OF THE INVENTION

The present invention provides a means by which magneto-therapeutic treatment can be applied to the eyes and/or face.

In one embodiment, an eye mask provides darkening coverage of the eyes and adjacent areas while providing magneto-therapeutic treatment thereto. An opaque eye mask has a perimeter cushion that serves to hold the mask from direct contact with the face and eyelashes. The mask generally covers the eyes from just above the eyebrows to just below the cheekbones and adjacent the temples. An elastic band or the like serves to secure the mask to the wearer's head. Magnets of alternating polarity are incorporated into the opaque portion of the eye mask serving to apply spatially alternating but static magnetic fields to the person's eyes and face.

In a second embodiment of the present invention, a full face mask is provided having apertures for the eyes, nose, and mouth. The mask fits over the entire face of the wearer and may also be secured to the head by means elastic bands or the like. Magneto-therapeutic treatment is provided by incorporating magnets of alternating polarity throughout the mask.

For both the eye mask and the face mask, the magnets of alternating polarity may comprise series of magnetic triangles of alternating polarity, magnetic squares of alternating polarity, and/or magnetic toroids with central circles of alternating magnetic polarity.

By donning either or both the magneto-therapeutic face mask and/or magneto-therapeutic eye mask of the present invention, a person can achieve magneto-therapeutic treatment to the face and/or eyes. As the eye mask or face mask may be passively secured to the head of the wearer, such may be worn while the person is sleeping without disturbing the sleep. The masks may also be used during other periods of continued repose or otherwise.

OBJECTS OF THE INVENTION

It is an object of the present invention to provide magneto-therapeutic treatment to a person's eyes.

It is an object of the present invention to provide magneto-therapeutic treatment to a person's face.

It is an additional object of the present invention to provide magneto-therapeutic treatment to the face and/or eyes through a series of spatially alternating but static magnetic fields.

It is an additional object of the present invention to provide magneto-therapeutic treatment without the use of active electrical sources.

These and other objects and advantages of the present invention will be apparent from a review of the following specification and accompanying drawings.

BRIEF DESCRIPTION OF THE DRAWINGS

FIGS. 4 and 5 show a checkerboard-type magnet configuration for use in the present invention.

DESCRIPTION OF THE PREFERRED EMBODIMENT(S)

As shown in the figures, the present invention provides masks by which certain portions of the face may be covered to thereby apply magneto-therapeutic treatment.

Figure 1:
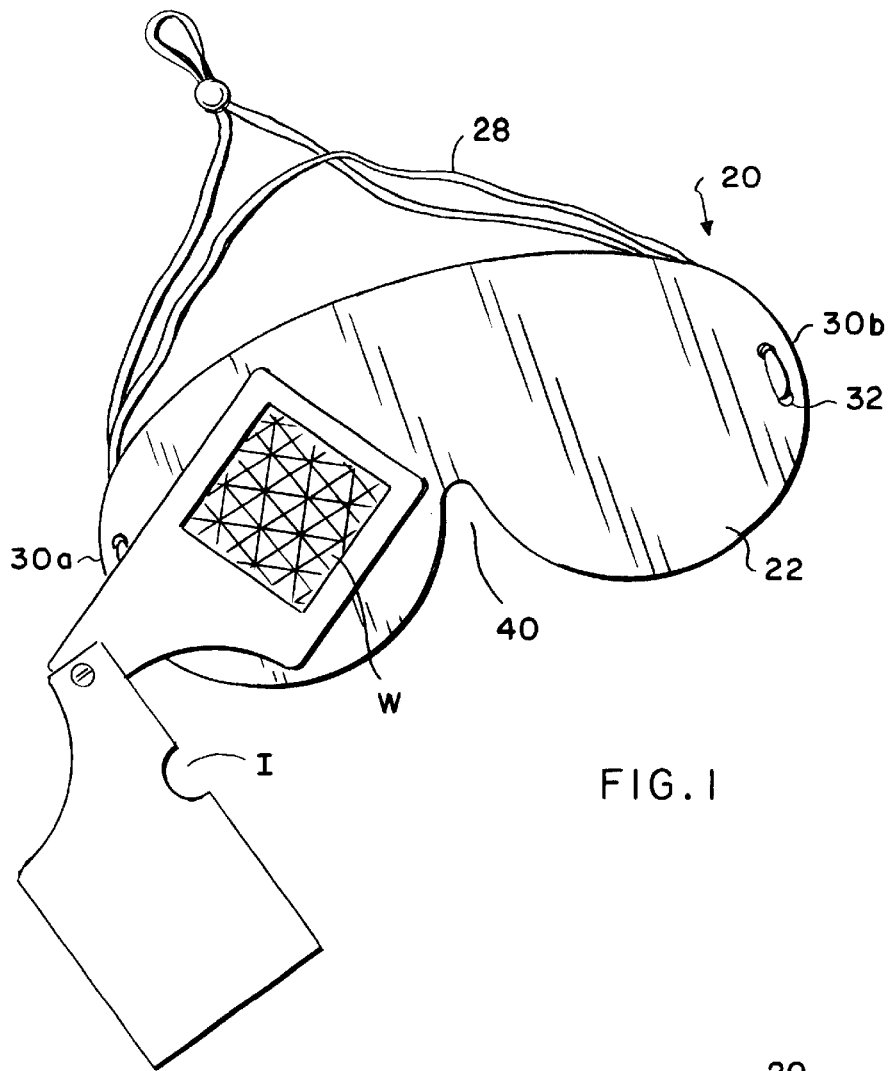
FIG. 1 shows a front perspective view of the eye mask of the present invention. A magnetic field indicator is shown adjacent the eye mask, indicating a first embodiment of the magnetic configuration.

In FIG. 1, an eye mask 20 serves to provide opaque covering for and magneto-therapeutic treatment to the eyes and adjoining areas of a person. The eye mask 20 has an opaque eye mask plate 22 which may be made of black plastic or the like. Behind the eye mask plate 22, towards the interior of the eye mask 20, is a sheet of alternating magnetic material 24. The alternating magnetic sheet 24 may be provided by a series of individual magnets of alternating polarity. The alternating magnetic sheet 24 may incorporate a soft backing or the like, closest to the eyes of the wearer of the eye mask 20.

Circumscribing the perimeter of the eye mask plate 22 is a cushion 26 or the like. The cushion 26 generally forms a light-impermeable barrier about the perimeter of the eye mask plate 22 when worn by a person. The cushion 26 may be formed of light and compressible foam rubber or the like and may project rearwardly from the eye mask plate 22 approximately one-half inch (½"). This projection of the cushion 26 serves to provide greater comfort for the wearer of the eye mask 20. As the foam rubber cushion 26 is opaque, it also tends to keep light out, thereby darkening the space defined between the cushion 26 and the eye mask plate 22 when the eye mask 20 is worn by the wearer.

Additionally, greater comfort is provided by the cushion 20 as it holds the eye mask plate 22 and alternating magnetic sheet 24 slightly away from the wearer's face. The eyelashes project outwardly from the eyelids, and there is a natural blinking reflex that tends to cause blinking whenever the eyelashes or portions adjacent the eye come into contact with any physical object. The perimeter cushion 20 holds the alternating magnetic sheet and eye mask plate sufficiently away from the eyes so as not to interfere with the travel of the eyelashes during blinks or the like. This prevents irritating distraction to the wearer when the eye mask 20 is worn.

In order to attach the eye mask 20 temporarily to the face, elastic straps or the like 28 are attached at far ends 30a, 30b of the eye mask 20. In one form, the elastic straps 28 may pass through holes 32 present in the eye mask plate 20 and alternating end cushion 26. With the presence of a pair of holes 32 at each end 30a, 30b of the eye mask plate 22, a single elastic strap may be looped through and back the holes 32 in order to provide dual elastic straps 28. By having a pair of elastic straps 28 attaching the eye mask 20 to the head, greater comfort and control are given to wearer as the attachment of the eye mask 20 to the face may be adjusted to a wider degree.

In order to take up any slack that may be present in the elastic strap 28, a constricting bead, buckle, or other device 32 may be used. By slidably adjusting the constricting bead 32 and adjusting the associated loop of material 34, increased tension may be applied to the elastic strap 28, thereby tightening the hold of the elastic strap 28 and the eye mask 20 upon the head of the wearer.

Figure 2:
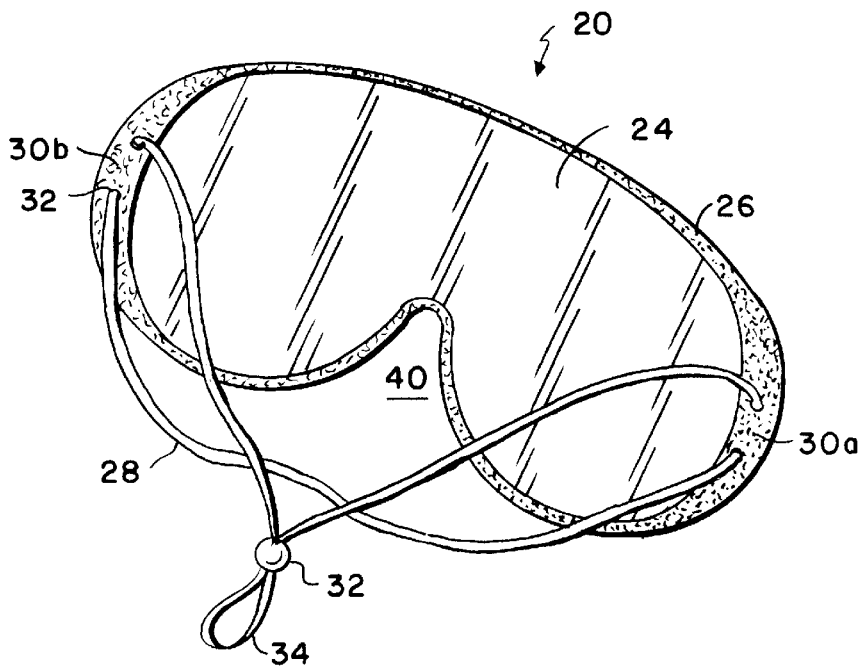
FIG. 2 shows a rear perspective view of the eye mask of FIG. 1.

As shown in FIGS. 1 and 2, the eye mask 20 generally takes the form of a pair of goggles or the like. As mentioned above, the eye mask plate 22 may be opaque, but this is not a requirement and translucent and transparent eye mask plates 22 fall within the contemplation of the present invention.

The eye mask 20 is meant to amply fit over the eyes of the wearer in order to provide a dark and magneto-therapeutic environment for the eyes and adjacent facial areas of the wearer. In order to do so, a nose notch 40 is present at the central lower portion of the eye mask 20 adjacent the nose notch 40. The cushion 26 serves as means by which the bridge of the nose and adjoining areas may be comfortably engaged by the eye mask 20 adjacent the nose notch 40. The individual lobes on either side of the nose notch 40 are sufficiently large to surround the eyes. In one embodiment, the eye mask 20 fits just over the brow of the wearer and travels adjacent the sides of the face near the temples before addressing the face just at or below the cheekbones. As mentioned above, the cushion 26 then travels about the perimeter of the nose notch 40 so that entire enclosure made by the cushioning perimeter gasket 26 distributes equal pressure about the perimeter of the eye mask 20 on the face of the wearer.

Figure 6:
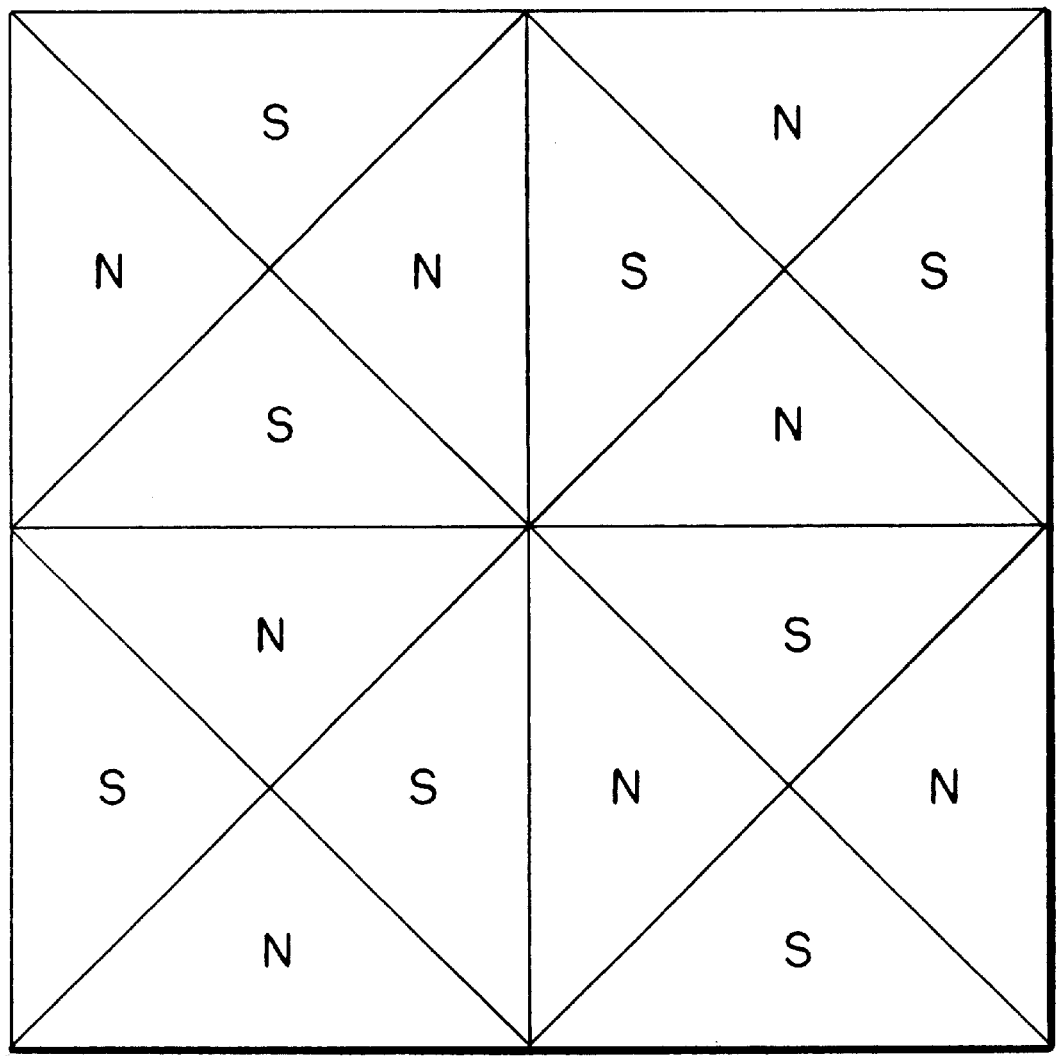
FIGS. 6 and 7 show a triangular checkerboard magnet configuration for use in the present invention.
Figure 7:
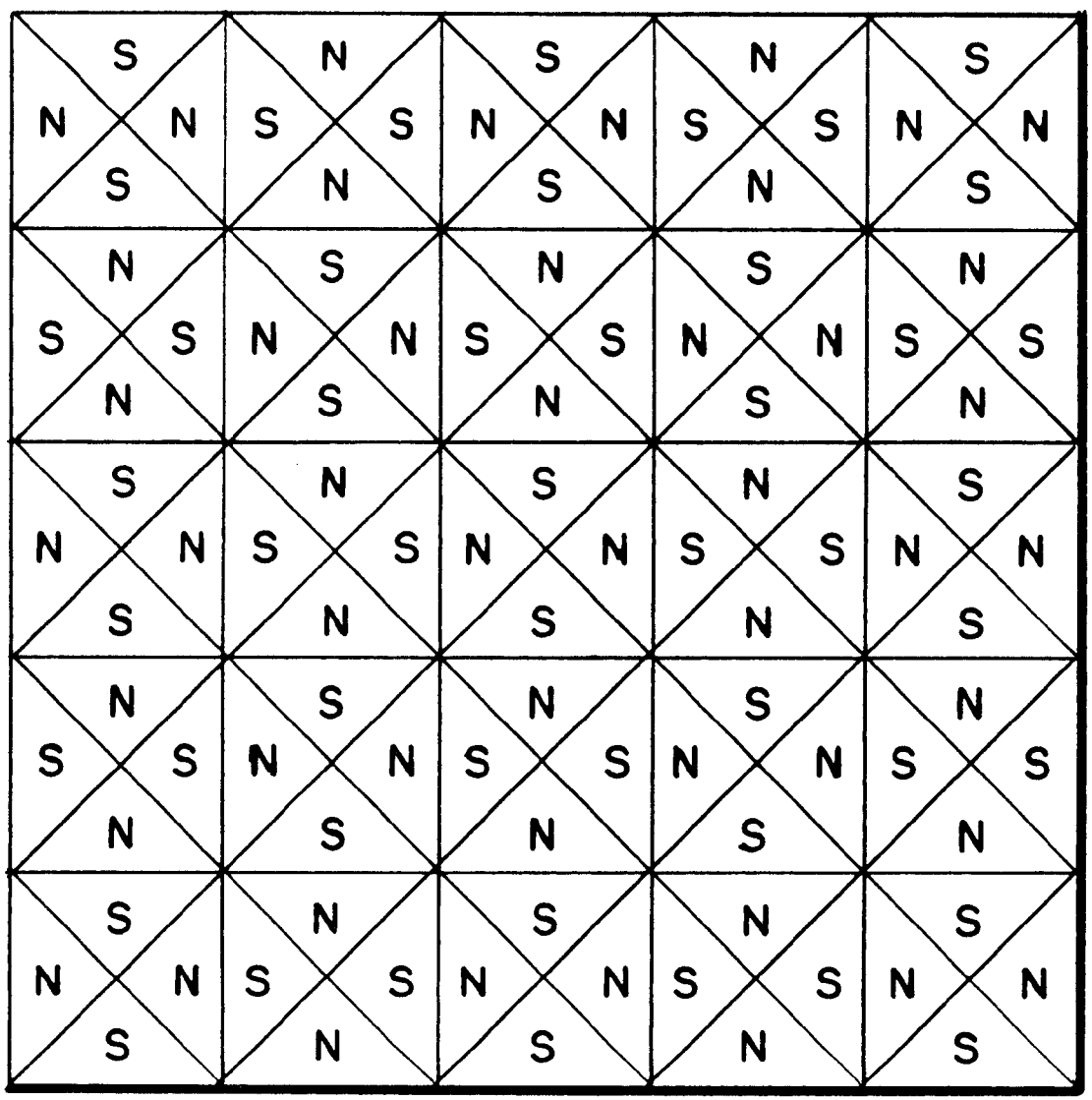

FIG. 1 shows a magnetic field indicator I with a viewing window W adjacent the front portion of the eye mask plate 22. As shown in the window W, the eye mask plate 22 covers an alternating magnetic sheet 24 having a series of triangular magnets in a close-fit checkerboard pattern. This is also shown in FIGS. 6 and 7 where adjacent triangles have opposite polarity to produce a spatially-alternating magnetic field.

In order to use the eye mask 20 as shown in FIGS. 1 and 2, the elastic bands 28 are pulled away from the rear of the eye mask 20 so that the head may fit between the elastic bands 28 and the eye mask plate 22 and perimeter cushion 26. Upon fitting the eye mask plate upon the head, the elastic straps 28 are adjusted for a snug fit that is comfortable upon the face of the wearer. Light is kept out by the opaque nature of both the eye mask plate 22 and the cushion 26. Magneto-therapeutic treatment is thereby effected upon the eyes and adjacent ocular areas which may be prolonged for a significant period if the eye mask 20 is donned prior to sleep or other lengthy repose.

Figure 3:
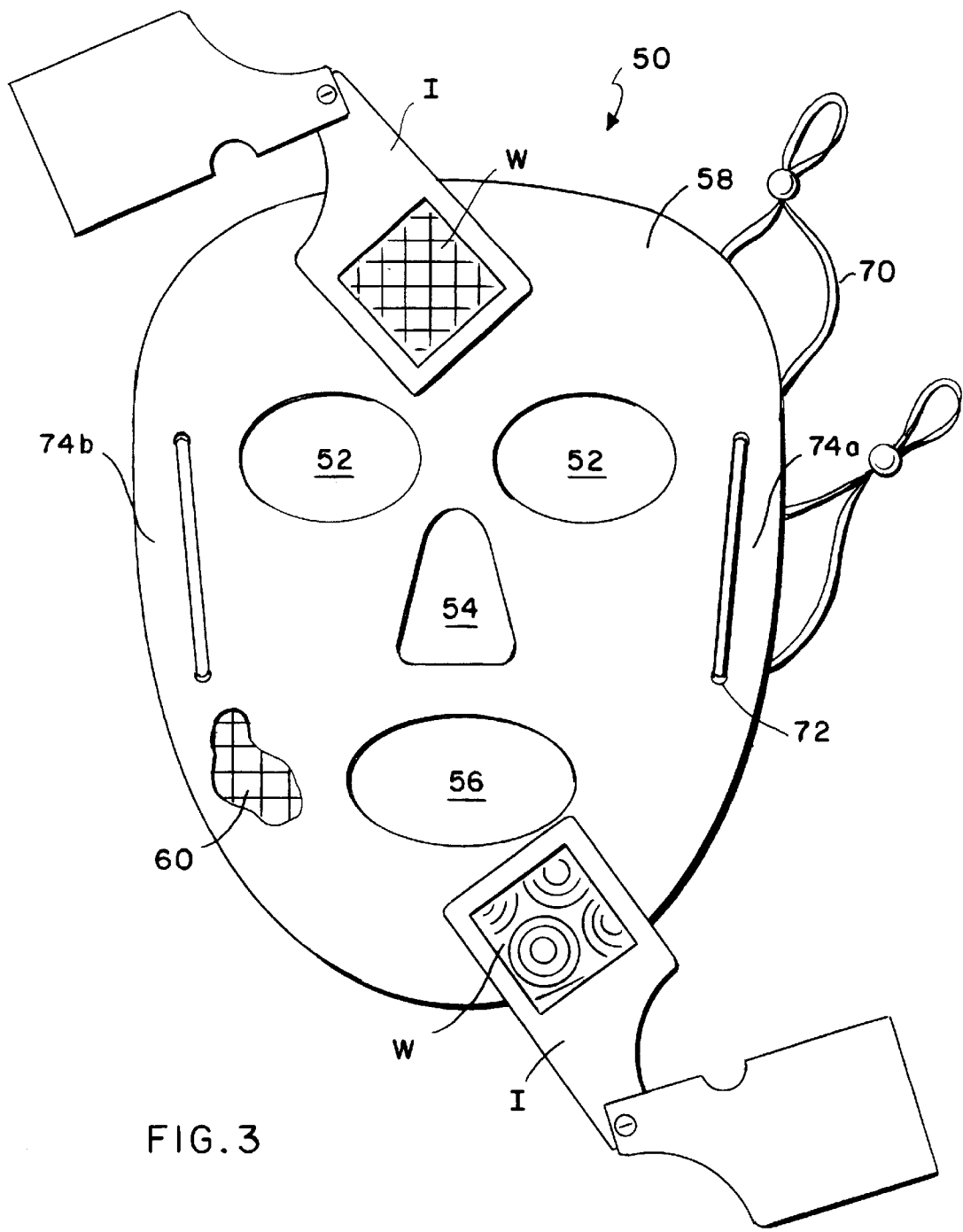
FIG. 3 shows a front perspective view of the face mask of the present invention with two magnetic indicators showing two alternative embodiments of the magnetic configuration used in the present invention.

As shown in FIG. 3, a face mask 50 is configured to generally cover the entire front area of the face. In the embodiment shown in FIG. 3, apertures are present for the eyes 52, nose 54, and mouth 56. In an alternative embodiment (not shown) the apertures for the eyes 52 may be omitted so that the eyes are also covered by the face mask 50. As with the eye mask 20, the face mask 50 should be somewhat flexible so that it can conform to the contours of the face.

The face mask may have an interior contact surface for the face of cloth, plastic, or other comfortable material. Bendable sheets having alternating magnetic polarity may be surrounded by the cloth exterior 58 in order to protect the alternating magnetic sheet 60 and to provide a comfortable surface with which the skin may come into contact. Elastic straps 70 serve to provide means by which the face mask 50 may be attached to the person's head. Strap holes or apertures 72 are present on the left and right sides 74a, 74b of the face mask 50. The elastic strap hole 72 may be vertically spaced apart so as to provide greater distribution of the holding force by the elastic strap 70 upon the person's face.

If the face mask 50 has no eye apertures 52, appropriate spacing should be made as by cushions or the like, in order to space the inner surface of the face mask 50 away from the batting eyelashes of the person. This prevents irritation and distraction as the eyelashes will come into contact with no foreign object. Alternatively, the area adjacent the eyes may be formed to accommodate the travel of eyelashes without interference. The nose 54 and mouth 56 apertures should be of sufficient dimension to allow appropriate accommodation of these anatomical structures.

As contemplated in the present invention, the face mask 50 covers the face from the top of the forehead along the sides of the face and temples down to the chin. Additional coverage of the neck, ears, and other related structures may be achieved by appropriate extensions of the alternating magnetic sheet material. Additionally, caps, hoods, or the like of alternating magnetic sheet material may provide application of spatially alternating but static magnetic fields to the skull, cranium, and other structures of the head.

As shown in FIG. 1, two magnetic field indicators I indicate different alternating magnetic sheet magnet structures in their windows W. In the upper indicator, a square checkerboard pattern is indicated in the window W. In the lower indicator I, a circular and toroidal pattern of alternating magnetic polarity is shown in the window W. In all embodiments of the present invention, the alternating magnetic sheet material may comprise magnets of several different types of materials, including barium ferrite polymer, strong nickel-cobalt magnets, or other magnetic materials. So long as the triangular or square checkerboard patterns, or circular/toroidal alternating magnetic polarity patterns, or the like, are achieved, spatially alternating but static magnetic fields may be applied to the eyes and/or face in order to achieve magneto-therapy treatment thereto.

Figure 4:
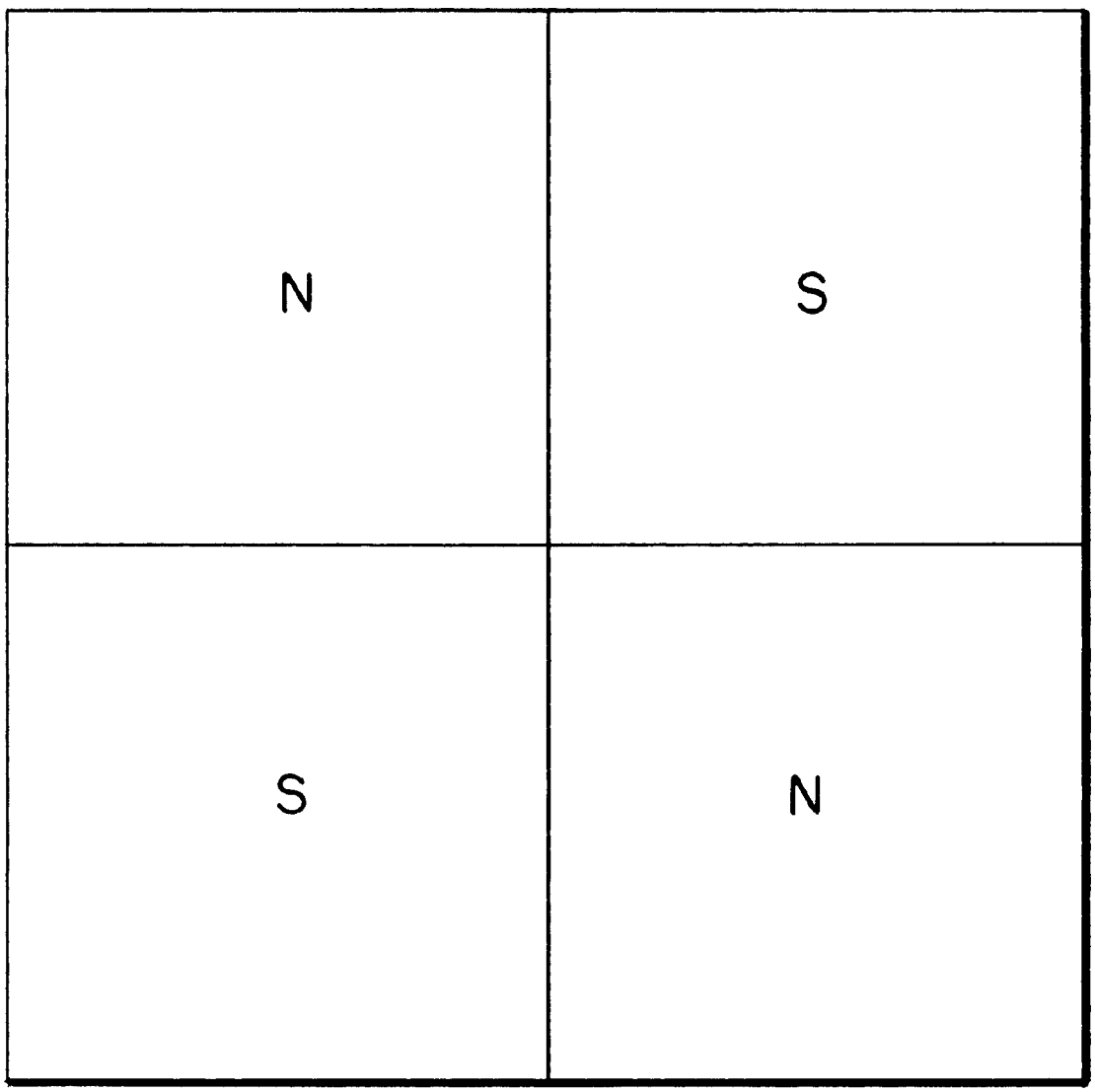
Figure 5:
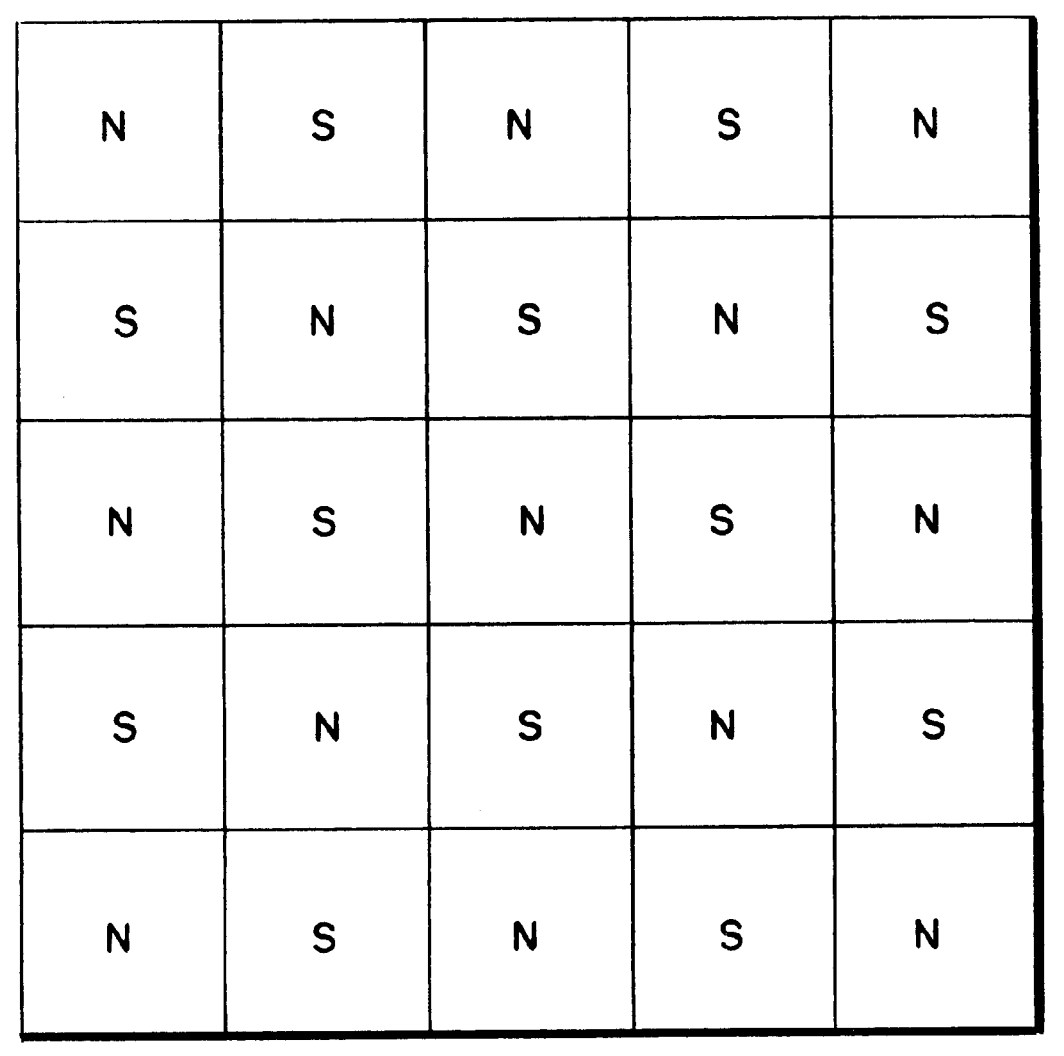
Figure 8:
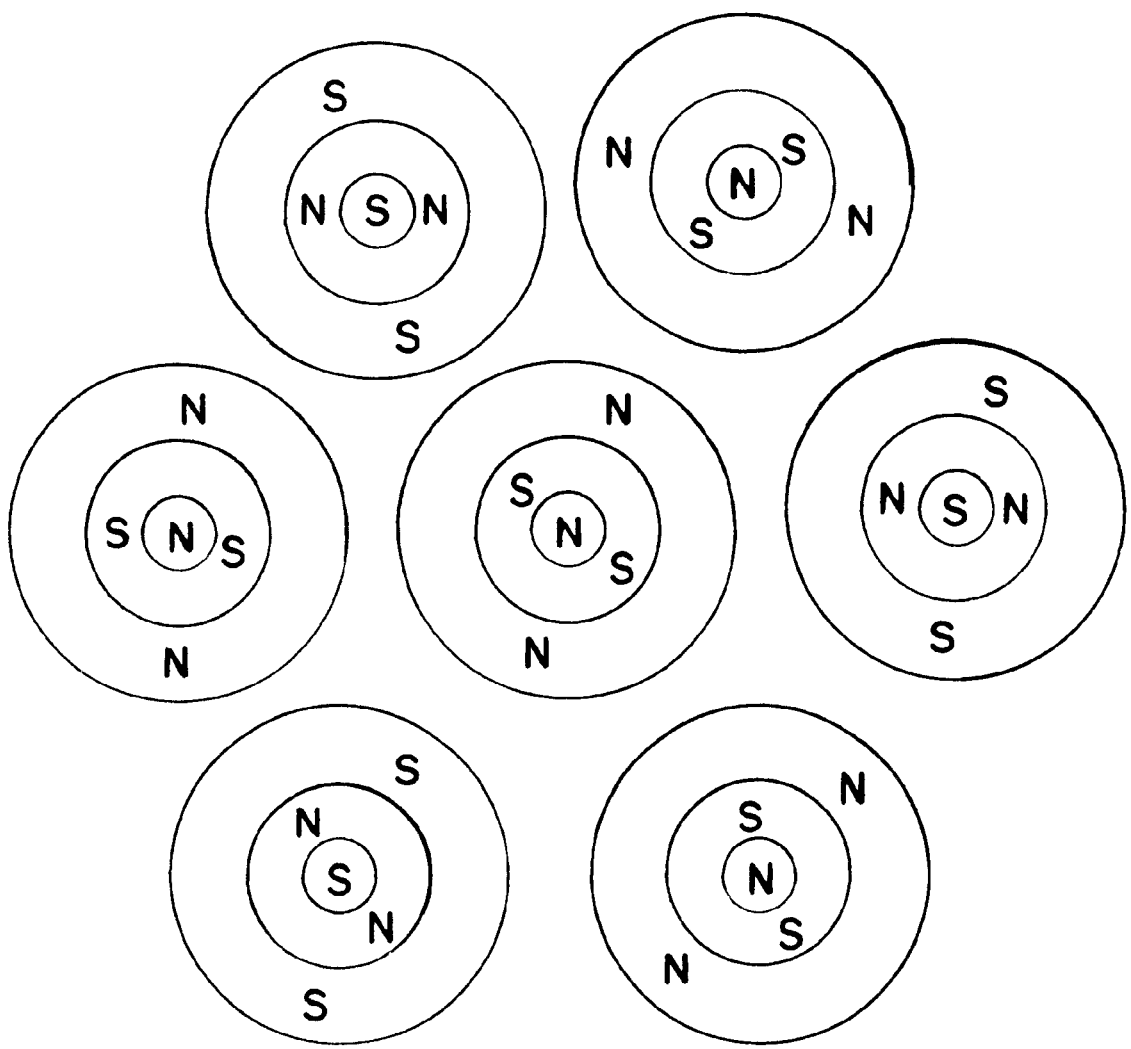
FIG. 8 shows a circular and toroidal magnet configuration for use in the present invention.

The square checkerboard alternating magnetic polarity pattern is shown in greater detail in FIGS. 4 and 5. The triangular checkerboard magnet pattern is shown in FIGS. 6 and 7. The circular and toroidal alternating magnetic polarity pattern is better shown in FIG. 8.

While the present invention has been described with regards to particular embodiments, it is recognized that additional variations of the present invention may be devised without departing from the inventive concept.

What is claimed is:

1. A magnetic mask for improving blood circulation adjacent a person's face, comprising:

a mask adapted to cover at least a portion of the face, said mask including an eye region adapted to cover the eyes of the person's face, said eye region opaque to prevent light from illuminating the person's eyes;

alternating contiguous magnetic surfaces having changes in magnetic polarity, where said contiguous alternating magnetic surfaces provide changes in magnetic polarity over a substantial portion of said mask; and attachment elements to attach said mask to the face; whereby a person donning the magnetic mask subjects the face to alternating magnetic polarity over a large uninterrupted magnetic region consequently stimulating ion-containing blood as it passes through changing magnetic fields over a large portion of the person's face.

2. The magnetic mask of claim 1, wherein said mask means further comprises a perimeter cushion circumscribing a perimeter of the magnetic mask, whereby said magnetic mask is held slightly away from the person's face for the person's greater comfort and to prevent interference with the free travel of blinking eyes or batting eyelashes.

3. The magnetic mask of claim 2, wherein said perimeter cushion is opaque and adapted to provide a light-tight seal between said eye mask and the person's face, whereby the person's eyes are held in darkness by said magnetic mask.

4. A magnetic mask for improving blood circulation adjacent a person's face, comprising:

an opaque eye mask adapted to cover the eyes of the person's face and preventing light from illuminating the person's eyes;

an opaque perimeter cushion circumscribing a perimeter of said eye mask, said perimeter cushion holding said eye mask slightly away from the person's face for the person's greater comfort, said perimeter cushion adapted to provide a light-tight seal between said eye mask and the person's face so that the person's eyes are held in darkness by the magnetic mask;

planar contiguous alternating magnetic surfaces having changes in magnetic polarity, where said planar contiguous alternating magnetic surfaces provide changes in magnetic polarity over a substantial portion of said opaque eye mask; and an adjustable elastic band adapted to adjustably attach said eye mask to the face; whereby a person donning the magnetic mask darkens the face and eyes and subjects said person to spatially contiguous alternating magnetic polarity over a large uninterrupted magnetic region consequently stimulating ferromagnetic ion-containing blood as it passes through changing magnetic fields over a large portion of the person's eyes and adjacent areas.

5. The magnetic mask of claim 4, wherein said planar alternating magnetic means comprises alternating magnetic triangles.

6. The magnetic mask of claim 4, wherein said planar alternating magnetic means comprises alternating magnetic squares.

7. The magnetic mask of claim 4, wherein said planar alternating magnetic means comprises series of concentric circles of alternating magnetic polarity.

* * * * *